(12) United States Patent
Matsuura

(10) Patent No.: US 8,439,827 B2
(45) Date of Patent: May 14, 2013

(54) ENDOSCOPE SYSTEM AND CONTROL METHOD FOR THE SAME

(75) Inventor: Hideo Matsuura, Saitama (JP)

(73) Assignee: Fujifilm Corporation, Tokyo (JP)

( * ) Notice: Subject to any disclaimer, the term of this patent is extended or adjusted under 35 U.S.C. 154(b) by 728 days.

(21) Appl. No.: 12/556,496

(22) Filed: Sep. 9, 2009

(65) Prior Publication Data

US 2010/0063355 A1  Mar. 11, 2010

(30) Foreign Application Priority Data

Sep. 10, 2008 (JP) ................ 2008-231890

(51) Int. Cl.
*A61B 1/04* (2006.01)
*A61B 1/06* (2006.01)

(52) U.S. Cl.
USPC ......................................... 600/118; 600/160

(58) Field of Classification Search .............. 600/103, 600/118, 160, 178; 348/45
See application file for complete search history.

(56) References Cited

U.S. PATENT DOCUMENTS

| | | | |
|---|---|---|---|
| 5,667,474 A | 9/1997 | Nishimura | |
| 6,570,615 B1 | 5/2003 | Decker et al. | |
| 7,745,771 B2 | 6/2010 | Troxell et al. | |
| 2003/0176768 A1 | 9/2003 | Gono et al. | |
| 2006/0149133 A1 | 7/2006 | Sugimoto et al. | |
| 2007/0014553 A1* | 1/2007 | Endo | 396/52 |
| 2008/0018733 A1* | 1/2008 | Hasegawa | 348/68 |

FOREIGN PATENT DOCUMENTS

| | | |
|---|---|---|
| JP | 1-280440 A | 11/1989 |
| JP | 6-062438 A | 3/1994 |
| JP | 6-327627 A | 11/1994 |
| JP | 7-246184 | 9/1995 |
| JP | 2002-95635 | 4/2002 |
| JP | 2004-321244 A | 11/2004 |
| JP | 2007-244681 A | 9/2007 |

OTHER PUBLICATIONS

U.S. Appl. No. 12/385,219, filed Apr. 1, 2009 (Hiroshi Yamaguchi, et al.).
Japanese Office Action dated Aug. 13, 2012 with a partial English translation thereof.
United States Office Action dated May 2, 2012, in U.S. Appl. No. 12/556,481.

(Continued)

*Primary Examiner* — Clayton E Laballe
*Assistant Examiner* — Minh Phan
(74) *Attorney, Agent, or Firm* — McGinn IP Law Group, PLLC

(57) ABSTRACT

In an endoscope, a solid-state image pickup device images an object, to output an image signal. In a processing apparatus, an illuminator applies normal light and specific light having spectral distribution different from the normal light to the object. A display control unit operates according to the image signal, to cause display of a normal image of the object produced by applying the normal light, and a specific image of the object produced by applying the specific light. A motion detector detects information of relative motion of the object. A controller controls the illuminator, causes alternate emission of the normal and specific light periodically at a storage period of the image pickup device if the motion information is equal to or smaller than a threshold level, and causes emission of the normal light without emitting the specific light if the motion information is greater than the threshold level.

8 Claims, 6 Drawing Sheets

OTHER PUBLICATIONS

United States Notice of Allowance dated Mar. 16, 2012, in U.S. Appl. No. 12/561,050.

Japanese Office Action dated Sep. 27, 2012 and English translation thereof.

United States Office Action dated Nov. 15, 2012, in U.S. Appl. No. 12/385,219.

* cited by examiner

Pc

ENDOSCOPE SYSTEM AND CONTROL METHOD FOR THE SAME

BACKGROUND OF THE INVENTION

1. Field of the Invention

The present invention relates to an endoscope system and a control method for the same. More particularly, the present invention relates to an endoscope system in which normal and specific light can be selectively utilized for precise imaging of an object in a body cavity, and a control method for the same.

2. Description Related to the Prior Art

An electronic endoscope is widely used for a diagnosis by medical examination in the field of medical instruments. The endoscope includes a head assembly for entry in a body cavity. A solid-state image pickup device is incorporated in the head assembly, such as a CCD image sensor and the like. There are a processing apparatus and a light source to both of which the endoscope is connected by use of a cable, connector or the like.

The processing apparatus processes an image signal from the image pickup device in processing of various functions, and produces image data of an endoscopic image for use in the diagnosis. A display panel in connection with the processing apparatus is driven to display the image. The light source contains a white light source such as a xenon lamp, and emits illumination light for application to an object in the body cavity.

The NBI (Narrow band imaging) is known in the field of the diagnosis by use of the endoscope to facilitate discovery of lesions. Specific light of a narrow wavelength of a predetermined band is applied to an object of interest, with a difference from normal light of white color characteristically having a broad wavelength. Reflected light of the specific light is evaluated for imaging of a specific image, which is distinct from a normal image obtained under a condition with the normal light. In the narrow band imaging (NBI), special images can be easily created without coloring the object with color dye, injection of angiography contrast medium such as indocyanine green (ICG), or the like, for example, the images with enhancement of submucosa blood vessels, and with enhancement of structures of organs such as stomach walls and surface tissue of intestines.

Specific methods of the narrow band imaging (NBI) are disclosed in U.S. Pat.Pub. No. 2003/176768 (corresponding to JP-A 2002-095635) and U.S. Pat. No. 5,667,474 (corresponding to JP-A 7-246184). An optical filter assembly for use includes a filter for the normal light and a filter for the specific light, and is disposed in a light path of the light from the light source. A motor or other mechanism shifts the filter assembly when an operator or doctor manually operates a button or the like for changeover, to create the normal and specific images by imaging.

U.S. Pat.Pub. No. 2003/176768 discloses use of a rotary filter in the endoscope for outputting the normal and specific light. In one embodiment of this document, elongation of the storage time of the image pickup device is suggested in imaging with the specific light for the purpose of compensating for reduction of an amount of light even upon changeover to the specific light. Blur of an image will occur seriously with the elongation of the storage time. In view of this, a motion detector for detecting motion of the object of interest is incorporated. If no motion is detected in a period of freeze-frame operation, an image in an image memory is renewed. If motion of the object is found, the renewal of the image memory is disabled. Furthermore, in a certain embodiment of the same document, a xenon lamp is suggested as light source of the normal light, a super high pressure mercury lamp is suggested as light source of the specific light.

U.S. Pat. No. 5,667,474 includes an optical instrument having the filter assembly and the motion detector in a manner similar to U.S. Pat.Pub. No. 2003/176768. If motion of the object of interest is detected before imaging with the normal light, the freeze-frame operation is disabled. If motion of the object is detected before imaging with the specific light, addition of preceding and succeeding frame images (noise reduction) is disabled. If no motion of the object is detected before imaging with the specific light, addition of preceding and succeeding frame images (noise reduction) is carried out.

In the narrow band imaging (NBI), it has been impossible in the diagnosis visually to compare the normal and specific images by simultaneous display on a display panel. This is due to a time difference between imaging of the normal and specific images. If the object of interest relatively moves between time points of the imaging of those, no simultaneity is kept between the two to cause failure in precise comparison.

In U.S. Pat.Pub. No. 2003/176768 and U.S. Pat. No. 5,667,474, the filter assembly is shifted mechanically to change over the display form of each of the normal and specific images in an exclusive manner. There is no suggestion of simultaneity, or closeness in the time of imaging of the normal and specific images. Although relative motion of the object of interest is detected, U.S. Pat.Pub. No. 2003/176768 only discloses determination of renewal of image data at the time of the freeze-frame operation. U.S. Pat. No. 5,667,474 only discloses inhibition of the freeze-frame operation and allowance of the noise reduction. Precise comparison between the normal and specific images is not suggested in known techniques of endoscope system.

SUMMARY OF THE INVENTION

In view of the foregoing problems, an object of the present invention is to provide an endoscope system in which normal and specific light can be selectively utilized for precise imaging of an object in a body cavity, and a control method for the same.

In order to achieve the above and other objects and advantages of this invention, an endoscope system includes a solid-state image pickup device for picking up an image of an object, to output an image signal. An illuminator applies normal light and specific light having a wavelength range different from the normal light to the object. A motion detector detects information of relative motion of the object. A controller controls the illuminator, causes alternate emission of the normal and specific light periodically at a storage period of the image pickup device if the detected motion information is equal to or smaller than a threshold level, and causes emission of the normal light without emitting the specific light if the detected motion information is greater than the threshold level. A display control unit causes display of a normal image produced from the image signal in applying the normal light, and additionally a specific image produced from the image signal in applying the specific light.

The illuminator includes a normal light source for emitting the normal light. A specific light source emits the specific light.

The display control unit causes display of a selected one of a set of motion pictures of the normal and specific images arranged together, and a motion picture of an overlay image of the normal and specific images.

In a preferred embodiment, the display control unit causes display of a selected one of a motion picture of the normal image in a discrete manner, a motion picture of the specific image in a discrete manner, a set of motion pictures of the normal and specific images arranged together, and a motion picture of an overlay image of the normal and specific images.

If the detected motion information is greater than the threshold, then the display control unit causes display of a motion picture of the normal image.

If the detected motion information is greater than the threshold, then the display control unit causes display of a motion picture of the normal image, and a still picture of the specific image under a condition of the controller upon turning off the specific light, in a form arranged together.

Also, the endoscope system includes an endoscope having the image pickup device. A processing apparatus has the illuminator incorporated therein. A cable connects the endoscope with the processing apparatus. A light guide device is disposed to extend through the cable and the endoscope, for passing the normal and specific light from the illuminator. A lighting window is formed in the endoscope, positioned in front of a distal end of the light guide device, for illuminating the object with the normal or specific light.

Furthermore, a first internal light guide device is disposed to extend from the normal light source. A second internal light guide device is disposed to extend from the specific light source. A coupler combines the normal and specific light from the first and second internal light guide devices to guide to the light guide device.

In a preferred embodiment, an endoscope system including an endoscope, an illuminator, a processing apparatus and a display panel is provided. The endoscope includes a solid-state image pickup device for picking up an image of an object to output an image signal. A light guide device illuminates the object. The illuminator includes a normal light source for emitting normal light for entry in the light guide device. A specific light source emits specific light having a wavelength range different from the normal light, for entry in the light guide device. The processing apparatus includes a motion detector for detecting information of relative motion of the object. A controller controls the illuminator, causes alternate emission of the normal and specific light periodically at a storage period of the image pickup device if the detected motion information is equal to or smaller than a threshold level, and causes emission of the normal light without emitting the specific light if the detected motion information is greater than the threshold level. A display control unit causes the display panel to display a normal image produced from the image signal in applying the normal light, and additionally a specific image produced from the image signal in applying the specific light.

In one aspect of the invention, a control method of controlling an endoscope system is provided, in which a solid-state image pickup device picks up image light from an object to output an image signal. In a lighting step, normal light and specific light having spectral distribution different from the normal light is applied to the object. In a display step, according to the image signal, a normal image of the object produced by applying the normal light, and a specific image of the object produced by applying the specific light, are displayed. In a detecting step, information of relative motion of the object is detected. There is a control step of control for causing alternate emission of the normal and specific light periodically at a storage period of the image pickup device if the detected motion information is equal to or smaller than a threshold, and for causing emission of the normal light without emitting the specific light if the detected motion information is greater than the threshold.

A selected one of a set of motion pictures of the normal and specific images arranged together, and a motion picture of an overlay image of the normal and specific images, is displayed in the display step.

Furthermore, a computer-executable program for controlling an endoscope system is provided, in which a solid-state image pickup device picks up image light from an object to output an image signal. The computer-executable program includes a lighting program code for applying normal light and specific light having spectral distribution different from the normal light to the object. A display program code is for, according to the image signal, displaying a normal image of the object produced by applying the normal light, and a specific image of the object produced by applying the specific light. A detecting program code is for detecting information of relative motion of the object. A control program code is for control for causing alternate emission of the normal and specific light periodically at a storage period of the image pickup device if the detected motion information is equal to or smaller than a threshold, and for causing emission of the normal light without emitting the specific light if the detected motion information is greater than the threshold.

Consequently, normal and specific light can be selectively utilized for precise imaging of an object in a body cavity, because motion of the object is evaluated and can be utilized for changeover of the normal and specific light.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
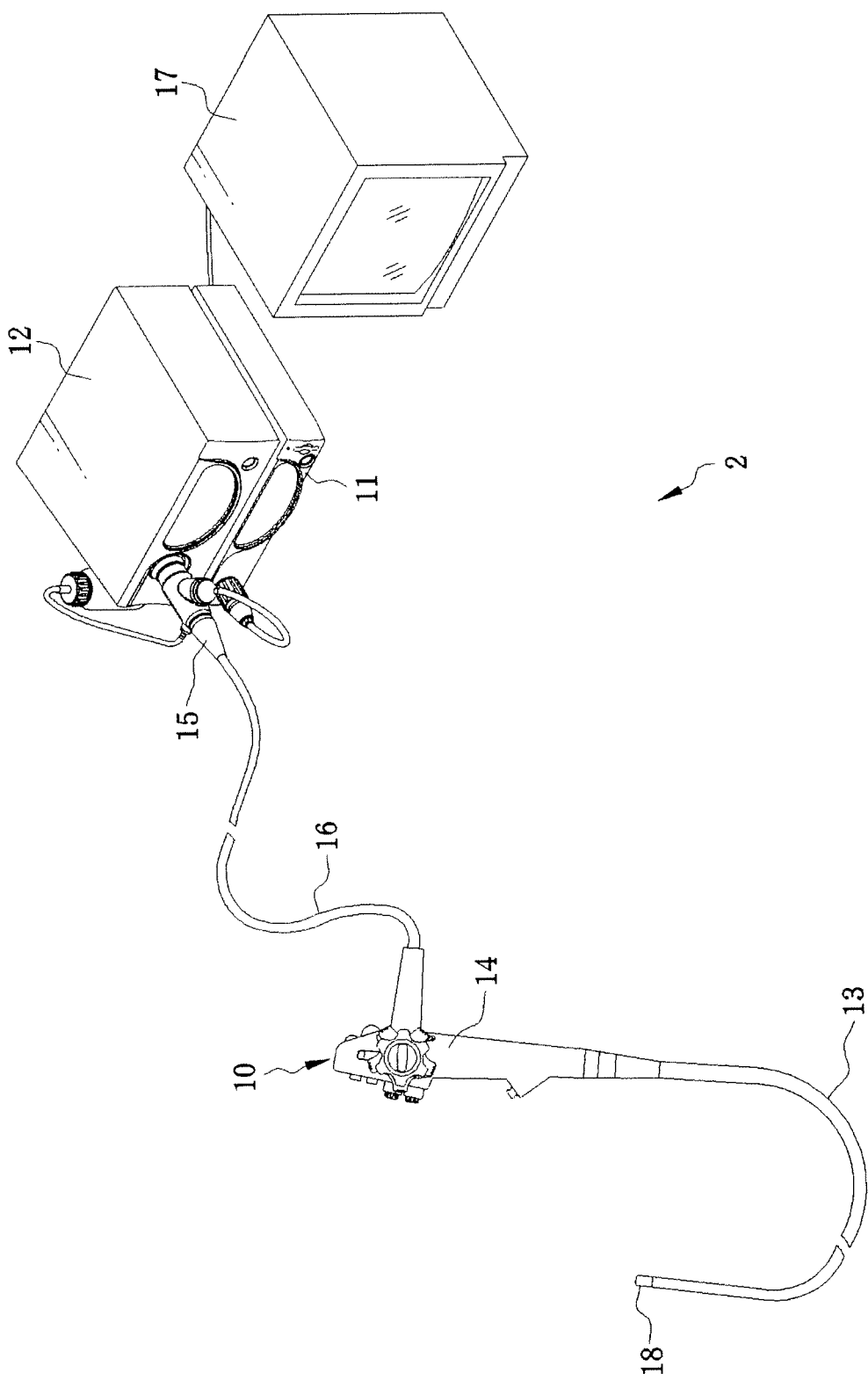
FIG. 1 is a perspective view illustrating an endoscope system.

In FIG. 1, an endoscope system 2 includes an electronic endoscope 10, a processing apparatus 11 and an illuminator 12 or light source. The endoscope 10 is a well-known instrument, and includes an insertion tube 13, a handle assembly 14, a connector 15 and a universal cable 16. The insertion tube 13 is entered orally in a gastrointestinal tract of a human body. The handle assembly 14 is a support from which the insertion tube 13 extends. The universal cable 16 extends from the handle assembly 14, and coupled with the connector 15 for connection to the processing apparatus 11 with the illuminator 12.

Figure 2:
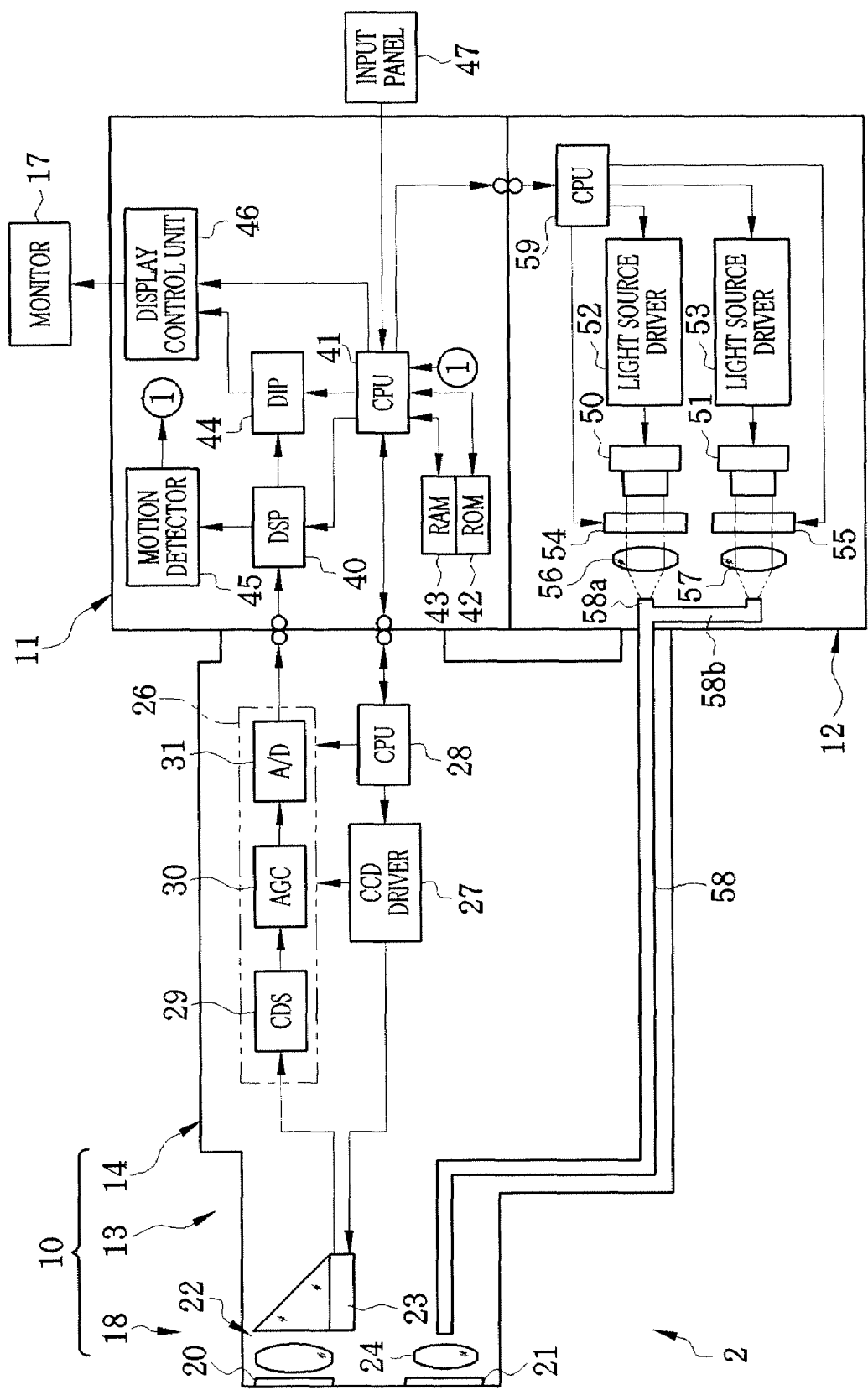
FIG. 2 is a block diagram illustrating the endoscope system.

A head assembly 18 is disposed at the end of the insertion tube 13. In FIG. 2, an imaging window 20 and a lighting window 21 are formed in an end face of the head assembly 18. A solid-state image pickup device 23 or CCD is incorporated in the insertion tube 13 behind the imaging window 20. An optical system 22 is disposed in front of the image pickup device 23. The lighting window 21 causes application of light to an object in the body cavity, the light being emitted by the illuminator 12 and guided by a light guide device 58 in the universal cable 16 and the insertion tube 13. There is a lighting lens 24 where the light passes.

The handle assembly 14 includes a steering wheel, an air/water supply button and a release button. The steering wheel is rotatable for steering the head assembly 18 on the insertion tube 13 up and down and to the right and left. The air/water supply button is depressible for sending air and/or water through the head assembly 18 on the insertion tube 13. The release button is operable for still picture recording of an endoscopic image.

A first forceps opening is formed in a face of the distal end of the handle assembly 14 for insertion of an electric blade or other tools. A second forceps opening is formed in the end face of the head assembly 18. A forceps channel is formed in the insertion tube 13 to extend from the first forceps opening to the second forceps opening.

The processing apparatus 11 is electrically connected with the illuminator 12, and controls the entirety of the endoscope system 2. Also, the processing apparatus 11 supplies the endoscope 10 with power by use of a transmission cable extending through the universal cable 16 and the insertion tube 13, and controls imaging of the image pickup device 23. The processing apparatus 11 receives an image signal output by the image pickup device 23 through the transmission cable, and produces image data by processing of the image signal. According to the image data produced by the processing apparatus 11, a display panel 17 is caused by the processing apparatus 11 to display an endoscopic image.

In the endoscope 10, the head assembly 18 at the end of the insertion tube 13 in FIG. 2 includes the imaging window 20, the lighting window 21, the optical system 22, the image pickup device 23 and the lighting lens 24. The handle assembly 14 contains an analog signal processor 26 (AFE), a CCD driver 27 and a CPU 28.

Examples of the image pickup device 23 are a CCD image sensor of an interline transfer type, CMOS image sensor and the like. Image light from an object in a body cavity is passed through the imaging window 20 and the optical system 22, and becomes incident upon a sensor surface of the image pickup device 23. The optical system 22 has lenses/lens groups and a prism. A color filter of plural color segments is disposed on the sensor surface of the image pickup device 23, for example, a primary color filter of the Bayer arrangement.

The AFE 26 includes a correlated double sampling circuit 29 (CDS), an automatic gain control unit 30 (AGC) and an A/D converter 31. The CDS 29 subjects the image signal from the image pickup device 23 to the correlated double sampling, and removes noise of the amplification and reset noise generated by the image pickup device 23. The AGC 30 amplifies the image signal after the noise reduction from the CDS 29 by use of an output gain which is determined by the processing apparatus 11. The A/D converter 31 converts the amplified image signal into a digital signal of a predetermined number of bits. The image signal in the digital form is sent by the universal cable 16 and the connector 15 and input to the processing apparatus 11. A working memory (not shown) of a digital signal processor 40 (DSP) is accessed and stores the digitalized image signal in a temporary manner.

The CCD driver 27 generates drive pulses for the image pickup device 23 and a sync pulse for the AFE 26, the drive pulses including vertical/horizontal scan pulses, reset pulse and the like. The image pickup device 23 picks up an image of an object in response to the drive pulses from the CCD driver 27, and outputs an image signal. The CDS 29, the AGC 30 and the A/D converter 31 of the AFE 26 operate according to the sync pulse from the CCD driver 27.

A control CPU 41 is incorporated in the processing apparatus 11. After the endoscope 10 becomes connected to the processing apparatus 11, the CPU 28 drives the CCD driver 27 according to a start signal from the control CPU 41, and adjusts an output gain of the AGC 30.

The control CPU 41 controls the entirety of the processing apparatus 11. Various circuit elements are connected to the control CPU 41 by a data bus (not shown), address bus, control lines and the like. A ROM 42 stores various programs (OS, application programs and the like) for control of the processing apparatus 11, and various data such as graphic data. The control CPU 41 reads required programs and data from the ROM 42. A RAM 43 is utilized as a working memory for the control CPU 41, to run the programs suitably. An input panel 47 is connected with the control CPU 41. The control CPU 41 receives information from the input panel 47, the LAN (local area network) and the like, and writes the information to the RAM 43, the information including date information of the diagnosis, alphanumeric personal information of a patient or doctor, and the like.

The digital signal processor 40 reads an image signal from its working memory as created by the AFE 26. The digital signal processor 40 subjects the image signal in signal processing of various functions, such as color separation, color interpolation, gain correction, white balance adjustment, gamma correction and the like, and produces image data. A digital image processor 44 (DIP) has a working memory (not shown). The image data from the digital signal processor 40 is written to the working memory. A motion detector 45 is supplied with the image data.

The image processor 44 is controlled by the control CPU 41 and carries out the image processing of various functions. In the image processor 44, image data is read from the working memory after processing in the digital signal processor 40. The image processor 44 processes the image data in the image processing of electronic zooming, color enhancement, edge enhancement and the like. A display control unit 46 is supplied with the image data processed by the image processor 44.

A VRAM in the display control unit 46 stores the processed image data from the image processor 44. The display control unit 46 is supplied with graphic data read by the control CPU 41 from the ROM 42 and the RAM 43. Examples of the graphic data include data of a display mask, alphanumeric information, GUI (graphical user interface) and the like. The display mask causes an effective area to appear by masking areas of inactive pixels of an endoscopic image. The alphanumeric information can be data of a date of the diagnosis, and personal information of a patient, operator and the like. The display control unit 46 processes image data from the image processor 44 by processing of display control, for example overlay processing of the display mask, alphanumeric information, GUI and the like, and graphic processing for display on the display panel 17.

The display control unit 46 reads image data from the VRAM, and converts the image data into a video signal according to the display format of the display panel 17, namely a component signal, composite signal or the like. Thus, the display panel 17 is caused to display an endoscopic image.

The motion detector 45 includes a frame memory for storing image data of two consecutive frame images from the digital signal processor 40. The motion detector 45 compares the image data of the two consecutive frame images read from the frame memory, and detects a motion vector of the object of interest according to a detecting method known in the art. For example, a pattern matching method is used. Pixels corresponding to one object are retrieved by evaluating the two consecutive frame images, so that a distance and direction of the pixels are obtained to detect information of a motion vector. The motion detector 45 supplies the control CPU 41 with information of a size of the motion vector, namely an amount of the relative motion of the object.

The input panel 47 is a user interface which may be an input panel disposed on a casing of the processing apparatus 11, or an input device such as a mouse, keyboard, and the like. The control CPU 41 controls various elements in the processing apparatus 11 in response to a signal input with the input panel 47.

Also, the processing apparatus 11 has a compressor, a media interface, and a network interface. The compressor compresses image data in a predetermined format, for example JPEG (Joint Photographic Experts Group). The media interface writes the compressed image data to a removable medium or data storage, such as CF card, magneto-optic (MO) optical disk, CD-R and the like. The network interface controls transmission and reception of data in connection with the LAN (local area network) or other network. Those are connected to the control CPU 41 by a data bus or the like.

The illuminator 12 includes a broad band normal light source 50 and a narrow band specific light source 51. Examples of the normal light source 50 are a xenon lamp, which emits normal light or light with a broad wavelength of colors from red to blue, and a white LED for white light. In contrast, examples of the specific light source 51 are a blue LED and laser diode (LD), which emit specific light or light with a narrow wavelength of a predetermined band. The specific light source 51 emits specific light of one or two or more of wavelengths of 450, 500, 550, 600 and 780 nm.

Light source drivers 52 and 53 drive respectively the normal and specific light sources 50 and 51. Aperture stop mechanisms 54 and 55 are disposed in front of respectively the normal and specific light sources 50 and 51. Condenser lenses 56 and 57 pass light from the normal and specific light sources 50 and 51 at amounts controlled by the aperture stop mechanisms 54 and 55. The light guide device 58 is supplied with the condensed light obtained by the condenser lenses 56 and 57 after passage of the aperture stop mechanisms 54 and 55.

A CPU 59 as controller is incorporated in the illuminator 12, communicates with the control CPU 41 in the processing apparatus 11, and controls the light source drivers 52 and 53 and the aperture stop mechanisms 54 and 55. Light is guided to the distal end of the light guide device 58, diffused by the lighting lens 24, and applied through the lighting window 21 to an object in a body cavity.

The light guide device 58 includes a plurality of optical fibers of quartz, which are collected and set in a form of bundle by winding of a retaining tape or the like. A first internal light guide device 58a and a second internal light guide device 58b are disposed on the exit side of the normal and specific light sources 50 and 51, and extend in the illuminator 12 to join by way of the light guide device 58 with a Y coupler according to the Y-coupling technique in the field of optical fibers.

There are two modes of imaging settable in the endoscope system 2, including a normal mode with normal light and a specific mode with specific light. To designate one of the modes, the input panel 47 is manually operated.

When the normal mode is set, the control CPU 41 causes the CPU 59 to control the light source drivers 52 and 53. The normal light source 50 is turned on. The specific light source 51 is turned off. Only normal light is applied to the object. When the specific mode is set, the normal and specific light sources 50 and 51 are driven alternately with one another periodically at the storage period of the image pickup device 23. The object is illuminated by the normal and specific light changed over repeatedly at the storage period of the image pickup device 23.

Figure 3:
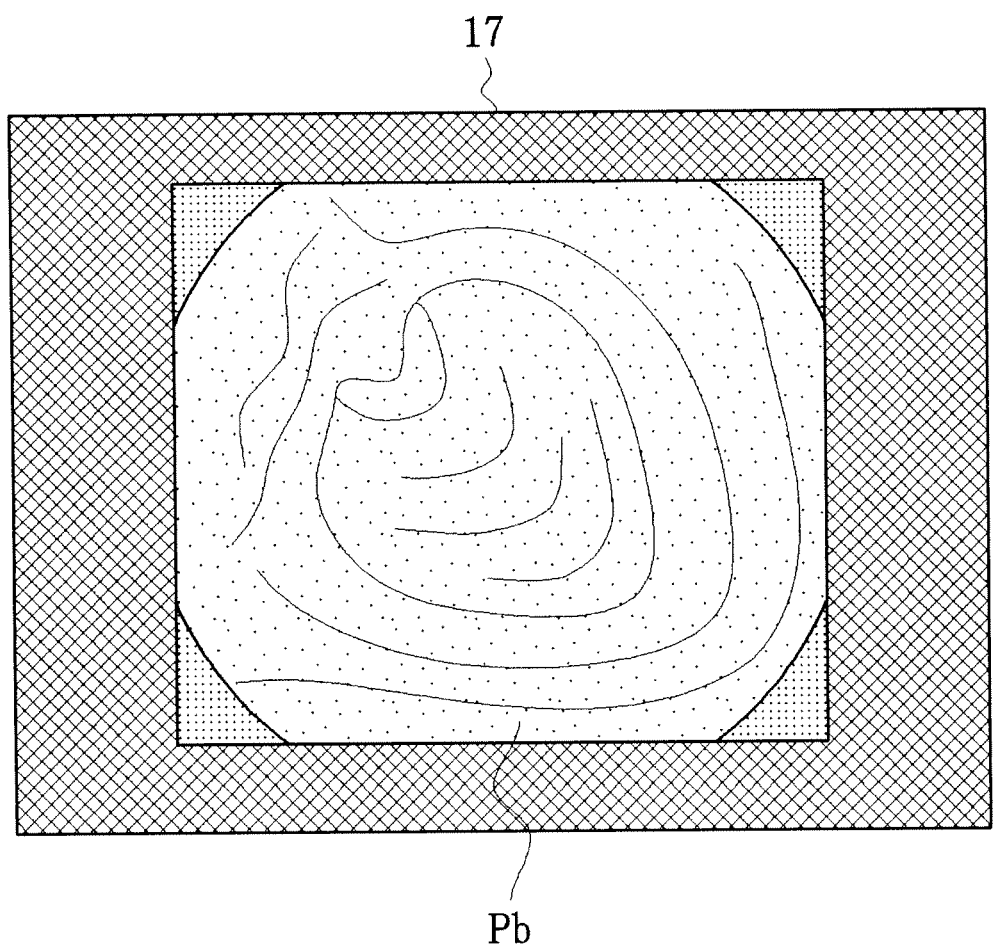
FIG. 3 is a plan illustrating a display form of an image in a specific mode.
Figure 4:
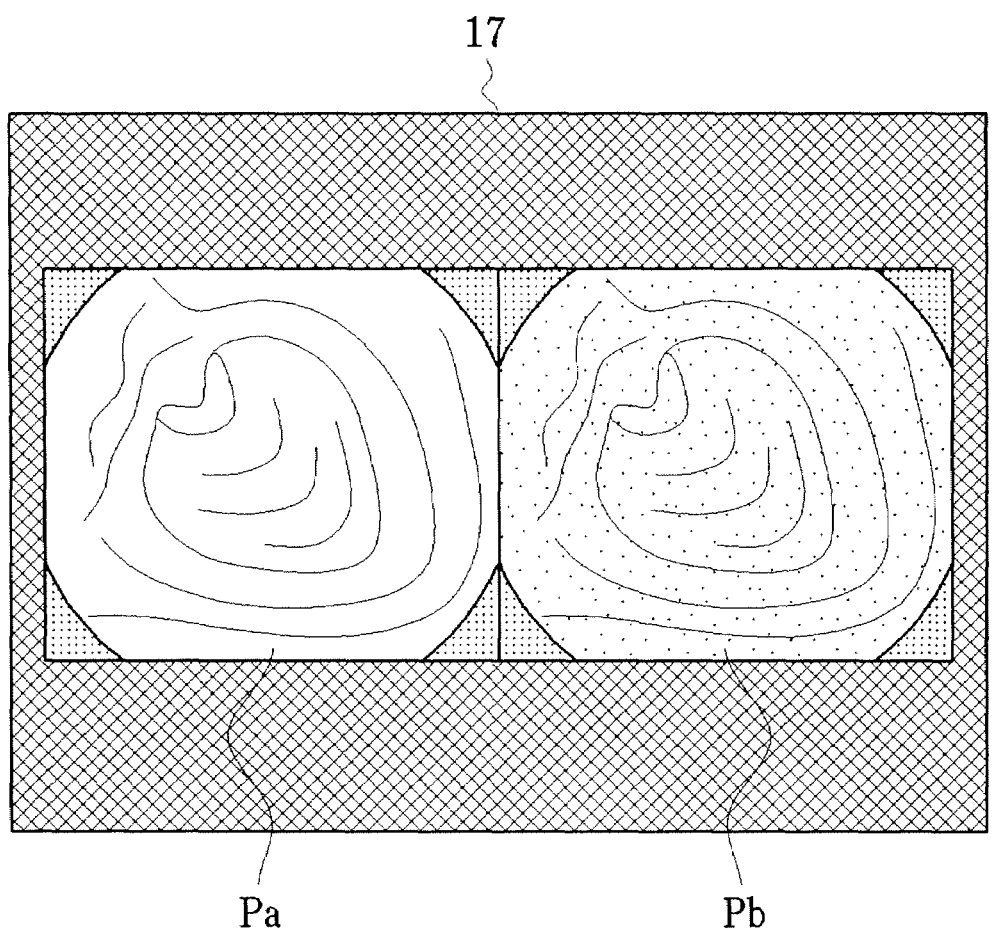
FIG. 4 is a plan illustrating a display form of images in the specific mode in a manner arranged together.
Figure 5:
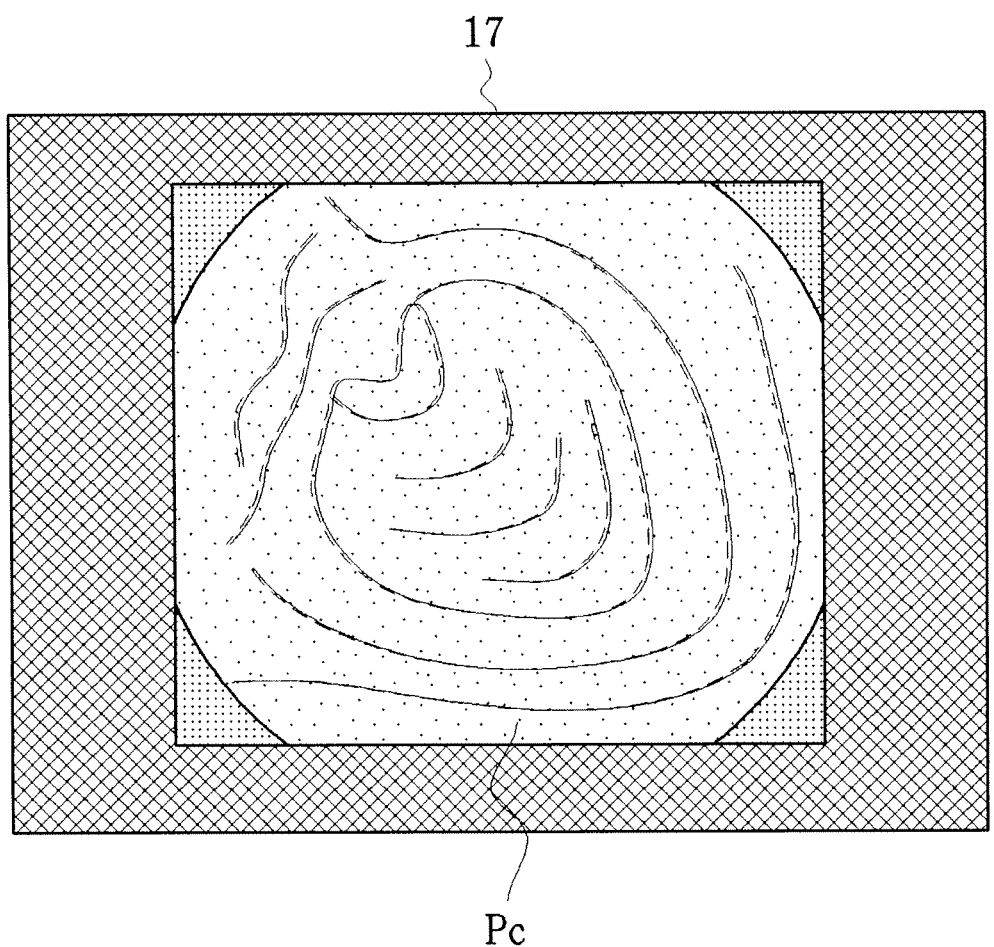
FIG. 5 is a plan illustrating a display form of an image in the specific mode as an overlay image.

In FIGS. 3, 4 and 5, display forms of the specific mode are illustrated. In FIG. 3, the display control unit 46 controls for displaying a motion picture of a specific image Pb generated by the digital signal processor 40 according to an image signal upon application of specific light to an object. In FIG. 4, the display control unit 46 controls for adjacently displaying a motion picture of the specific image Pb and a motion picture of a normal image Pa generated by the digital signal processor 40 according to an image signal upon application of normal light to the object. In FIG. 5, the display control unit 46 controls for displaying a motion picture of an overlay image Pc which is created by overlaying the normal and specific images Pa and Pb. Note that the display forms are changed over by operating the input panel 47. In the normal mode, a motion picture of the normal image Pa is displayed on the display panel 17. It is possible in the specific mode to display a motion picture of the normal image Pa. However, a frame rate of images in the specific mode is ½ as high as that of images in the normal mode.

When the specific mode is set and if the motion information is equal to or smaller than a threshold, then there is no change in the status of the control CPU 41, owing to a relatively small speed of the object of interest. Also, the normal and specific light sources 50 and 51 turn on and off alternately and periodically at the storage period of the image pickup device 23. There is no difference in the display form of an image with the display control unit 46 from the manner designated with the input panel 47.

If the motion information is greater than the threshold, namely if the relative speed of the object is comparatively high, then the control CPU 41 causes the CPU 59 to control the light source driver 53. The specific light source 51 is turned off to extinguish specific light. Only normal light is applied in the same manner as the normal mode.

In case of the display form of FIG. 3 of the motion picture of the specific image Pb, only normal light is applied. Then the display form is changed over automatically to the state of the normal mode. Only the motion picture of the normal image Pa is displayed on the display panel 17. In case of the display form of FIG. 5 of the motion picture of the overlay image Pc, there is no overlay of the specific image Pb. Then the display form is changed over to the state of the normal mode. However, it is necessary to prevent a drop of the frame rate as much as ½ in comparison with the frame rate of the normal mode, because the lack of one frame image occurs in association with the specific image Pb. Therefore, the display control unit 46 controls the display panel 17 to display images of image data input by the image processor 44 in the same manner as the normal mode.

If the display form is the adjacent display form of the normal and specific images Pa and Pb in FIG. 4, the display form is changed over to a motion picture of the normal image Pa by the same changeover as that from he display forms of FIGS. 3 and 5. Otherwise, a specific image (still picture) upon turning off specific light is displayed on the display panel 17 with the control CPU 41 without change while the normal image Pa of FIG. 4 remains displayed as a motion picture. The second of those display forms can be used in the case of the display form of FIG. 5.

The operation of the endoscope system 2 is described now. For endoscopic imaging of an object in a body cavity, a doctor or operator connects the endoscope 10 to the processing apparatus 11 and the illuminator 12. The processing apparatus 11 and the illuminator 12 are powered by turning on. The input panel 47 is operated to input personal information of the patient, and to start the diagnosis.

After the command signal for starting the diagnosis is output, the doctor or operator enters the insertion tube 13 in a body cavity. An object of interest is illuminated with light from the illuminator 12, while he or she observes an image on the display panel 17 upon imaging of the object with the image pickup device 23.

The image signal from the image pickup device 23 is processed by the CDS 29, the AGC 30 and the A/D converter 31 in the AFE 26, and input to the digital signal processor 40 of the processing apparatus 11. The digital signal processor 40 processes the image signal for signal processing of various functions, and produces image data. The image data is output to the image processor 44 and the motion detector 45.

The image processor 44 is controlled by the control CPU 41 and processes the image data from the digital signal processor 40 by image processing. The processed image data is input by the image processor 44 to the VRAM of the display control unit 46. The display control unit 46 carries out the display processing according to the graphic data from the control CPU 41. In response, the display panel 17 displays an endoscopic image of the image data.

When the normal mode is set by operating the input panel 47, the control CPU 41 controls for turning on the normal light source 50 and turning off the specific light source 51. Only normal light is applied to the object. Only a motion picture of the normal image Pa is displayed on the display panel 17.

Figure 6:
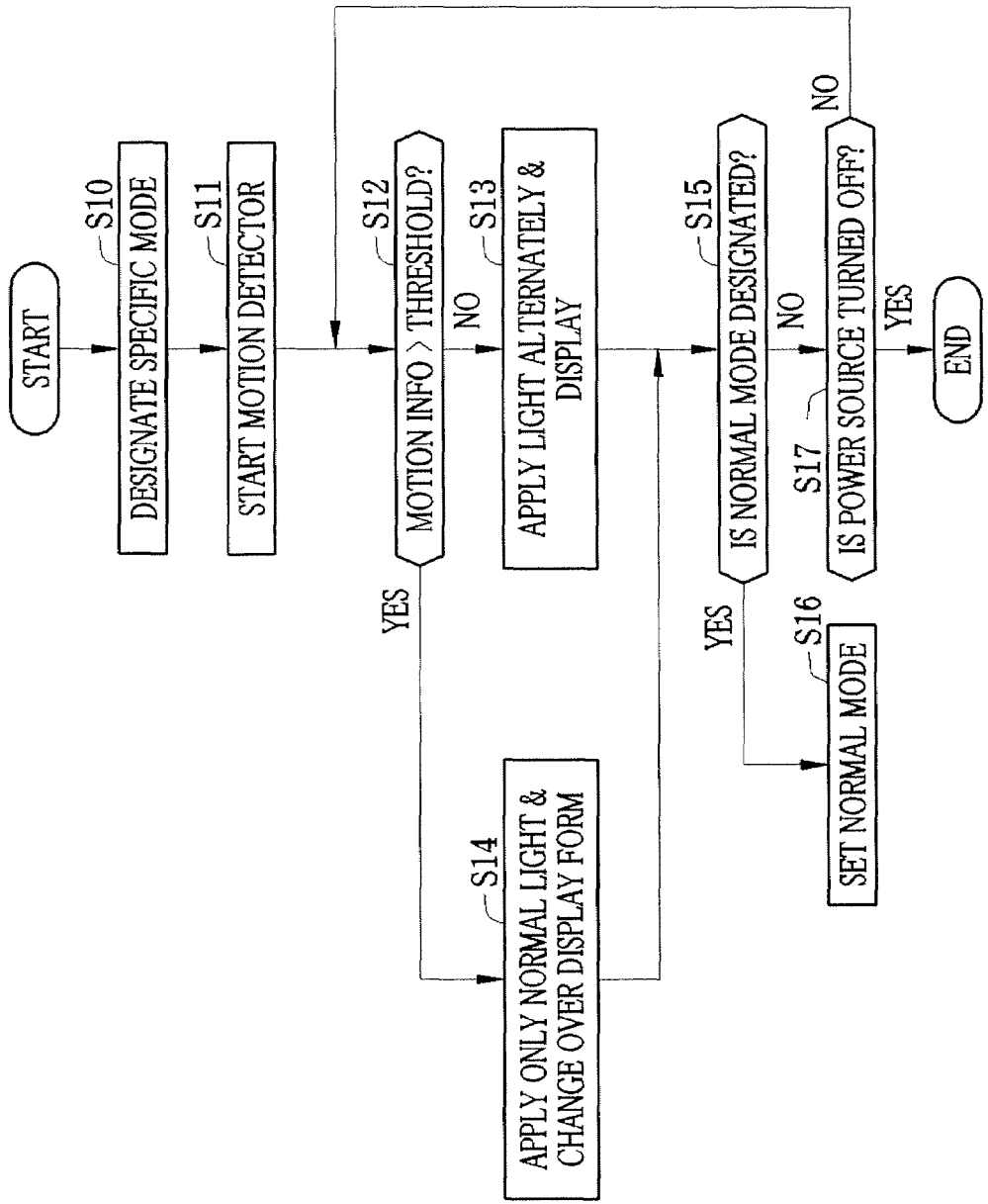
FIG. 6 is a flow chart illustrating a sequence of processing in the specific mode.

In the step S10 of FIG. 6, the input panel 47 is operated to set the specific mode. Then the motion detector 45 is started for detection in the step S11. Motion vector as motion information is generated by the motion detector 45 and input to the control CPU 41, and compared with the threshold for the evaluation.

If the motion information from the motion detector 45 is equal to or smaller than the threshold (NO in the step S12), then the control CPU 41 controls the normal and specific light sources 50 and 51 for alternate lighting periodically at the storage period of the image pickup device 23. Normal and specific light is applied to an object of interest at the storage period of the image pickup device 23. An image is displayed on the display panel 17 in the display form designated with the input panel 47.

If the motion information from the motion detector 45 is greater than the threshold (YES in the step S12), then the control CPU 41 turns off the specific light source 51 in the step S14 to extinguish the specific light. In the same manner as the normal mode, only normal light is applied to the object. Also, the display form is changed over to the form in the normal mode, or to a display form in which the normal image Pa appears as a motion picture, and the specific image Pb is adjacent with the normal image Pa as a still picture at the time shortly before extinguishing specific light in control of the control CPU 41. A sequence of those steps is repeated until the normal mode is designed (YES in the step S15) to set the normal mode (S16), or until the power source is turned off (YES in the step S17).

In short, the specific light is turned off by the control CPU 41 when the motion information is greater than the threshold according to the detection of relative motion of an object in the motion detector 45. Thus, the normal image Pa and specific image Pb on the display panel 17 can be simultaneous with one another in the time sequence.

Should the motion information from the motion detector 45 be greater than the threshold, the object of interest moves at a relatively high speed, to cause image blur between the normal and specific images Pa and Pb. However, it is possible in the invention to prevent degradation of images, such as failure in the color registration of the overlay image Pc and low sharpness of the contour of the object. This is because the overlay of the specific image Pb is canceled upon turning off specific light if the motion information from the motion detector 45 is greater than the threshold. In the case of having displayed motion pictures of the normal and specific images Pa and Pb adjacently, display of the specific image Pb is canceled, or a still picture of the specific image Pb is displayed. This is effective in automatically notifying the operator of impropriety of adjacent display of images for the diagnosis.

If the object moves at a relatively high speed, the insertion tube 13 is supposedly caused to travel in the body cavity according to operation of an operator of the endoscope 10. Specific light can be turned off if the motion information from the motion detector 45 is greater than the threshold, because the imaging or diagnosis is not essential in the course of travel of the insertion tube 13, and no influence will occur.

If the object moves at a relatively low speed owing to the motion information equal to or smaller than the threshold, the head assembly 18 on the insertion tube 13 is supposedly caused to reach a lesion or an object of interest to enable fully precise imaging. Then normal and specific light is applied alternately and periodically at the storage period of the image pickup device 23, so as to display a motion picture of the specific image Pb, display the motion pictures of the normal and specific images Pa and Pb adjacently, or display the overlay image Pc. Thus, it is possible to output images suitable for diagnosis in a timely manner for the operator's intention.

In the adjacent display form, a still picture of the specific image Pb is displayed. The overlay image Pc can be displayed always without an error in the color registration, color blur of the contour or other errors. Thus, there is no unwanted alteration in the appearance of the image in view of impression to eyes of the operator, patient or other persons.

When the motion information from the motion detector 45 is greater than the threshold, the display form is changed over to that of the normal mode. This is effective in raising quality of images in comparison with the conventional display form, because of smoothness of motion pictures with a high frame rate and the like.

If the motion information from the motion detector 45 is equal to or smaller than the threshold, the normal and specific light is applied alternately and periodically at the storage period of charge of the image pickup device 23. The normal and specific images Pa and Pb are output alternately frame by frame. A frame memory of the motion detector 45 stores only the normal images Pa, namely the new normal image Pa and the previous normal image Pa which is two images before the new normal image Pa. The specific image Pb is abandoned as an image between the new normal image Pa and the previous normal image Pa. The motion detector 45 detects a motion vector according to the two normal images Pa. It is to be noted that a motion vector may be detected from a relationship between a new specific image Pb and a previous specific image Pb.

Should the motion information fluctuate in the vicinity of the threshold quickly, it is likely that the light emission or display form changes excessively rapidly. In view of this, it is preferable to determine a sampling rate of the motion detector 45 at a suitable level. Also, it is preferable to change over the light emission when the motion information from the motion detector 45 is within the range of the threshold ±α, or change over the light emission with hysteresis effects after comparison of the motion information from the motion detector 45 with the threshold.

In the embodiment, the motion detector 45 is a single unit. In place of this, motion information can be detected by use of the DSP 40, DIP 44 or the like. Furthermore, a triaxial acceleration sensor or angular velocity sensor (gyro sensor) may be incorporated in the head assembly 18 at the end of the insertion tube 13, to detect motion information of the motion of the head assembly 18 relative to an object of interest.

In the embodiment, the normal and specific light sources 50 and 51 are used to emit normal and specific light. However, the invention is not limited to this embodiment. For example, it is possible to use an LED or LD of which a wavelength of oscillation of light is changeable according to a drive current. This is effective in saving the manufacturing cost and size of the space, as the light source can be single.

Also, a disk shaped filter or filter turret may be used, inclusive of a first filter portion for normal light and a second filter portion for specific light. The filter turret can be disposed in a light path of the light source, and rotated in a direction for the two filter portions to pass the light path alternately and periodically at the storage period of the image pickup device 23. Also, the filter turret may consist of an adapter removably attached to the head assembly 18 at the end of the insertion tube 13. This makes it possible in the invention to utilize a conventional endoscope system including a xenon lamp or white light source only with a small change in a computer program or the like.

In the embodiment, the light guide device 58 is single. However, two light guide devices may be incorporated and associated with respectively the normal and specific light sources 50 and 51.

Also, the normal and specific images Pa and Pb can be combined and displayed according to a display method of a picture-in-picture (PinP or PIP) form, in which a main display area and a sub display area are indicated.

In the embodiment, the control CPU 41 is a controller or master in the system. However, the CPU 59 may operate by way of this controller in the illuminator 12. The control CPU 41 supplies the CPU 59 with motion information generated by the motion detector 45, and compares the motion information from the motion detector 45 with the threshold. The display control unit 46 is controlled by the control CPU 41 to change over the display form. The CPU 59 of the illuminator 12 carries out the comparison in the manner of the control CPU 41, and causes the light source drivers 52 and 53 to change over the light emission.

Furthermore, the threshold may be variable, and may be set according to a setting of the input panel 47. An active or inactive state of changeover of the light emission or display form may be selectable in the case of selecting the specific mode. It is possible to use the endoscope system in compliance with an operator's intention.

Furthermore, it is possible to turn off the normal light source 50 and turn on the specific light source 51 if display of the motion picture of the specific image Pb is designated in the specific mode, instead of alternate emission of the normal and specific light sources 50 and 51. This makes it possible to obtain the specific image Pb for all of frame images.

The endoscope 10 of the invention may be an ultrasound endoscope in place of the electronic endoscope of the embodiment. Also, the light source may be incorporated together with the processing apparatus in a single apparatus of a composite form, instead of the separate structures of the two.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system, comprising:
    a solid-state image pickup device for picking up an image of an object, to output an image signal;
    an illuminator for applying a normal light and a specific light having a wavelength range different from said normal light to said object;
    a motion detector for detecting information of a relative motion of said object by comparing image signals of two frame images output from said solid-state image pickup device;
    a controller for controlling said illuminator, for causing alternate emission of said normal and specific light periodically at a storage period of said image pickup device if said detected motion information of the relative motion of said object is equal to or smaller than a threshold level, and for causing emission of said normal light without emitting said specific light if said detected motion information of the relative motion of said object is greater than said threshold level;
    a display control unit for causing display of a normal image produced from said image signal in applying said normal light, and additionally a specific image produced from said image signal in applying said specific light,
    wherein, if said detected motion information is greater than said threshold level, then said display control unit causes a display of a motion picture of said normal image, and a still picture of said specific image under a condition of said controller shortly before turning off said specific light, in a form arranged together.

2. An endoscope system as defined in claim 1, wherein said illuminator includes:
    a normal light source for emitting said normal light; and
    a specific light source for emitting said specific light.

3. An endoscope system as defined in claim 1, wherein said display control unit causes display of a selected one of a set of motion pictures of said normal and specific images arranged together, and a motion picture of an overlay image of said normal and specific images.

4. An endoscope system as defined in claim 1, wherein said display control unit causes display of a selected one of a motion picture of said normal image in a discrete manner, a motion picture of said specific image in a discrete manner, a set of motion pictures of said normal and specific images arranged together, and a motion picture of an overlay image of said normal and specific images.

5. An endoscope system, including:
    an endoscope;
    an illuminator; and
    a processing apparatus and a display panel,
    said endoscope including:
        a solid-state image pickup device for picking up an image of an object to output an image signal; and
        a light guide device for illuminating said object,
    said illuminator including:
        a normal light source for emitting normal light for entry in said light guide device; and a specific light source for emitting specific light having a wavelength range different from said normal light, for entry in said light guide device, and said processing apparatus including:
a motion detector for detecting information of a relative motion of said object by comparing image signals of two frame images output from said solid-state image pickup device;
a controller for controlling said illuminator, for causing alternate emission of said normal and specific light periodically at a storage period of said image pickup device if said detected motion information of the relative motion of said object is equal to or smaller than a threshold level, and for causing emission of said normal light without emitting said specific light if said detected motion information of the relative motion of said object is greater than said threshold level; and
a display control unit for causing said display panel to display a normal image produced from said image signal in applying said normal light, and additionally a specific image produced from said image signal in applying said specific light,
wherein, if said detected motion information is greater than said threshold level, then said display control unit causes a display of a motion picture of said normal image, and a still picture of said specific image under a condition of said controller shortly before turning off said specific light, in a form arranged together.

6. A control method of controlling an endoscope system in which a solid-state image pickup device picks up an image of an object for display on a display panel, said control method comprising:
detecting information of a relative motion of said object by comparing image signals of two frame images output from said solid-state image pickup device;
causing alternate emission of normal light and specific light having a wavelength range different from said normal light periodically at a storage period of said image pickup device if said detected motion information of the relative motion of said object is equal to or smaller than a threshold level, emission of said normal light being caused without emitting said specific light if said detected motion information of the relative motion of said object is greater than said threshold level; and
causing said display panel to display a normal image produced from said image signal in applying said normal light, and additionally a specific image produced from said image signal in applying said specific light,
wherein, if said detected motion information is greater than said threshold level, then in said display, a motion picture of said normal image, and a still picture of said specific image under a condition of said controlling shortly before turning off said specific light, are displayed in a form arranged together.

7. A control method as defined in claim 6, wherein a selected one of a set of motion pictures of said normal and specific images arranged together, and a motion picture of an overlay image of said normal and specific images, is displayed in said display.

8. A control method as defined in claim 6, wherein a selected one of a motion picture of said normal image in a discrete manner, a motion picture of said specific image in a discrete manner, a set of motion pictures of said normal and specific images arranged together, and a motion picture of an overlay image of said normal and specific images, is displayed in said display.

* * * * *